United States Patent [19]

Suroff

[11] Patent Number: 5,150,492
[45] Date of Patent: Sep. 29, 1992

[54] ULTRASONIC TOOTHBRUSH

[76] Inventor: Leonard W. Suroff, 12 Tompkins Ave., Jericho, N.Y. 11753

[21] Appl. No.: 652,628

[22] Filed: Feb. 8, 1991

[51] Int. Cl.⁵ .................. A61C 17/32; A46B 13/02
[52] U.S. Cl. .................. 15/22.1; 15/22.2; 318/118
[58] Field of Search ............ 15/22 R, 22.2; 318/116, 318/118; 128/62 A

[56] References Cited

U.S. PATENT DOCUMENTS

| | | | |
|---|---|---|---|
| 2,435,421 | 2/1948 | Blair | 15/23 |
| 3,335,443 | 8/1967 | Parisi et al. | 15/22.1 |
| 3,375,820 | 4/1968 | Kuris et al. | 15/22.1 |
| 3,809,977 | 5/1974 | Balamuth et al. | 15/22.1 |
| 3,840,932 | 10/1974 | Balamuth et al. | 15/22.1 |
| 3,941,424 | 3/1976 | Balamuth et al. | 15/22.1 |
| 3,980,906 | 9/1976 | Kuris et al. | 15/22.1 |
| 4,192,035 | 3/1980 | Kuris | 15/22.1 |
| 4,333,197 | 6/1982 | Kuris | 15/22.1 |
| 4,845,795 | 7/1989 | Crawford et al. | 15/22.1 |
| 4,991,249 | 2/1991 | Suroff | 15/22.2 |

Primary Examiner—Edward L. Roberts

[57] ABSTRACT

An ultrasonic toothbrush for use in personal dental hygiene care includes an exchangeable ultrasonic implement which may be rigidly and removably mounted to ultrasonic power means and readily removed therefrom with a relatively small separating force. Provision is made for coupling the toothbrush to the power means and is arranged to transfer the ultrasonic energy from the power means to the ultrasonic implement with the power means remaining substantially free from absorbing ultrasonic energy as the vibratory energy is transmitted therethrough.

55 Claims, 4 Drawing Sheets

ULTRASONIC TOOTHBRUSH

BACKGROUND OF THE INVENTION

1. Field of the Invention

The present invention relates to apparatuses for the cleaning of teeth, and more particularly, to an apparatus for personal dental care employing ultrasonic energy wherein the toothbrush implement may be readily removed and exchanged.

2. Discussion of the Relevant Art

It has been established that significant benefits are derived from regular dental care performed in the home by the individual himself together with periodic examination and treatment by professionally trained dentists. It is universally recognized, for example, that regular brushing of the teeth, particularly after every meal, serves to dislodge food particles which ordinarily are retained adjacent the teeth and which, if allowed to remain, would cause decay and dental caries. When properly administered, regular brushing also services to maintain good circulation in gingival tissue, thereby lessening the likelihood of gingival disease, one of the prime causes of premature loss of teeth. Perhaps of less, but nevertheless significant, importance are the stain removal and brightening actions resulting from regular brushing, which contribute noticeably to the appearance of the individual.

The present invention has found that, when applied under proper control to tooth and gingival surfaces in the human mouth, ultrasonic energy may be successfully employed for regular oral hygienic care without any damage to tooth surfaces or gingival tissues. These ultrasonic cleaning techniques provide a significantly increased cleaning ability, particularly in the interproximal and gum line areas where presently known brushing techniques are inadequate. Briefly, in accordance with the present invention, a cleaning member or oral contact portion, which preferably includes a plurality of individual cleaning elements, such as the bristles on a brush, is vibrated at an ultrasonic rate and manually moved over tooth and gingival surfaces under relatively light pressure.

Although not necessarily limited thereto, the combined ultrasonic and manual movement of the cleaning member may be performed in the presence of a fluid, such as water added specifically for the purpose, or in the natural fluids present in the human mouth and in the presence of dentifrices such as toothpaste. The unique properties displayed at the tips of an ultrasonically vibrating member such as a brush, enable greatly improved cleaning results to be achieved, particularly in areas where manual or conventional motor driven toothbrushes cannot reach. The ultrasonic energy is applied to the tooth and gingival surfaces such that no damage whatsoever to the surfaces will result. On the other hand, because of the greatly improved cleaning power, the buildup of tartar and scale deposits in the interproximal and gingival areas is significantly lessened, promoting a much higher degree of dental health than is possible with ordinary methods of dental hygienic care.

The art includes many different devices designed specifically to provide a means for dislodging food particles which may be retained between the teeth or removing deposits of plaque, tartar and scale occurring on the teeth. However, it appears that none of the devices in the prior art utilize an ultrasonic driving motor, that is a motor having vibratory output energy between 20,000 and 50,000 cycles per second (20-50 KHz) that are capable of transferring this ultrasonic vibratory force to the appliance or implement such as a toothbrush or other element, that is the utilizer of this energy, while permanently affixing the magnetostrictive or piezoelectric component to the appliance and permitting ready interchangeability of the toothbrush assembly or other element in a convenient manner for the end user.

Thus, when it becomes necessary to exchange the appliance, such as a toothbrush, so that different individuals utilizing the apparatus may readily utilize their own toothbrush or the toothbrush has to be replaced due to wear, it is ideal to change the toothbrush together with the magnetostrictive component, which forms a unitary assembly. In this way the vibratory forces can be transferred from the ultrasonic power source to the toothbrush, instrument, tool, etc. However, for individuals to use an ultrasonic toothbrush they must be able to exchange the toothbrush implement with ease and a minimal amount of force. Young children must be able to exchange the toothbrush implement with ease if the apparatus is to become popular.

Heretofore, one was not able to rigidly and removably mount a sealed exchangeable ultrasonic implement to ultrasonic power means wherein the vibratory energy may be transmitted to the toothbrush. The instant invention overcomes the shortcomings known in the prior art by providing a sealed ultrasonic power source and a sealed ultrasonic implement including a magnetostrictive element and toothbrush which may be quickly connected and disconnected to the ultrasonic power source with a relatively small separating force therebetween.

OBJECTS OF THE INVENTION

Therefore, it is an object of the present invention to provide a simple, efficient, reliable means of transferring ultrasonic energy from a power source to a replaceable implement adapted to vibrate at an ultrasonic rate.

It is another object of the present invention to provide an ultrasonic implement that may be rigidly and removably mounted on an ultrasonic power source and removed therefrom with a relatively small separating force.

It is yet another object of the present invention to provide a quick disconnect sealed ultrasonic implement for use with an ultrasonic power source that is efficient and is capable of transferring the vibratory energy from the power source to the ultrasonic implement.

SUMMARY OF THE INVENTION

An ultrasonic toothbrush apparatus, according to the principle of the present invention comprises, in combination, a sealed exchangeable ultrasonic implement such as a toothbrush, an ultrasonic power means for supplying vibratory energy in the ultrasonic range and an arrangement for rigidly and removably mounting the exchangeable ultrasonic implement with the ultrasonic power means with less than one complete revolution and with a relatively small separating force therebetween.

The apparatus in accordance with the invention is comparable in size and configuration to conventional motor driven toothbrush implements and is eminently suitable for home use by adults and children alike without special knowledge or training. The unit is constructed basically of two elements. The first, is the exchangeable ultrasonic implement which includes a cleaning member or brush that may take several different forms but in general is similar to conventional toothbrush heads, having a base member onto which are affixed a plurality of bristles or bristle-like elements. The elongated body portion is rigidly affixed, such as by epoxy, to one end of a narrow, elongated magnetostrictive material, which can be made to expand and contract at ultrasonic frequencies In the illustrated embodiments, the elongated member is completely enclosed and sealed in a nonmagnetic, material such as plastic, and forms with the brush head the ultrasonic implement or assembly which approximate the size and shape of an ordinary manual toothbrush.

The second element of the apparatus is the ultrasonic power means which is of a size and shape to be held conveniently in the hand of the user. The ultrasonic power means includes an elongated hollow housing having an axial bore or opening for receiving in close fitting engagement the ultrasonic implement inserted therein. There is provided means for rigidly and removably mounting the exchangeable toothbrush implement relative to the ultrasonic power means to prevent removal during use, but to allow ready removal by hand with a relatively small separating force. Alternating electrical signals are supplied to suitable elements within the ultrasonic power means or handle member to drive the vibrating element. With the ultrasonic implement positioned in the power means and alternating electrical signals at an ultrasonic frequency supplied thereto from an oscillator of convenient form, longitudinal vibrations are induced in the transducer portion of the ultrasonic implement, which in turn vibrates the toothbrush. As a result of the unique mounting arrangement, none of the vibratory energy or heat from the ultrasonic implement is transmitted to the housing.

In family use for example, a single power means and oscillation generator would be supplied, together with a number of ultrasonic implements, one for each member of the family. Each user simply inserts his own personal ultrasonic implement into the power means prior to cleaning his or her teeth.

The foregoing and other objects and advantages will appear from the description to follow. In the description, reference is made to accompanying drawing which forms a part hereof, and in which is shown, by way of illustration, specific embodiments in which the invention may be practiced. The embodiments will be described in sufficient detail to enable those skilled in the art to practice the invention, and that it is to be understood that other embodiments may be utilized and that structural changes may be made without departing from the spirit and scope of the invention. The following detailed description is, therefore, not to be taken in a limiting sense, and the scope of the present invention is best defined by the appended claims.

In the drawings, like reference characters have been utilized to designate like or corresponding components in the alternative embodiments of the invention in order to better understand the invention.

The following detailed description is, therefore, not to be taken in a limited sense wherein like reference numerals refer to like parts through the several views, and the scope of the present invention it is best to find by the appended claims.

BRIEF DESCRIPTION OF THE DRAWING

In order that the invention may be more fully understood, it will now be described, by way of example, with reference to the accompanying drawing in which.

DESCRIPTION OF THE PREFERRED EMBODIMENTS

Figure 1:
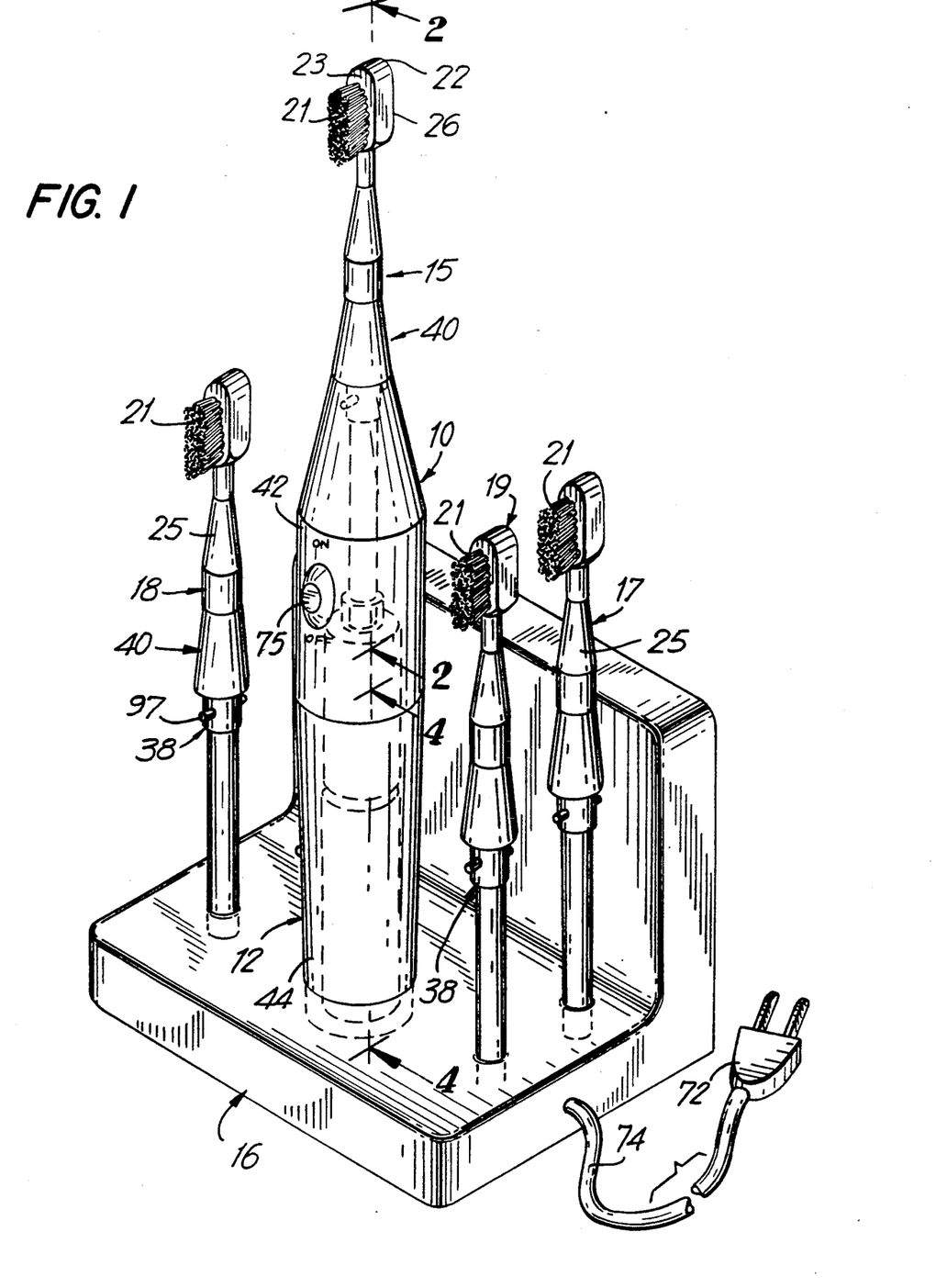
FIG. 1 is a perspective pictorial representation of an ultrasonic toothbrush in accordance with the present invention.

Referring now to the Figures, and in particular, to FIGS. 1 through 5, there is shown an ultrasonic toothbrush assembly or unit 10, constructed basically of two elements, an ultrasonic power means or handle 12 and an exchangeable ultrasonic toothbrush implement 15. The toothbrush assembly 10 is nested on a recharging base member 16 that also includes additional toothbrush implements elements 17, 18 and 19 that may be positioned thereon. Although only three toothbrushes are shown in FIG. 1, it is apparent that any number of toothbrushes may be provided as needed.

The toothbrush apparatus 10 in accordance with the invention is comparable in size and configuration to conventional motor driven toothbrushes and is eminently suitable for home use by adults and children alike without special knowledge or training. The implement 15 is shown in cross-section view in FIG. 2. The quick release ultrasonic implement or toothbrush 15 may take several different forms but in general is similar to conventional toothbrush heads, and includes an elongated body portion 20 fabricated of a non-magnetic vibration transmitting material having on one distal end an element, which may be in the form of bristles 21, disposed on a brush head 22. The brush head 22 may have a front surface or face 23 and parallel spaced apart sides or surfaces 24 and a rear or back surface 25 with a top surface 26 that blends with the surfaces 23, 24 and 25, respectively. The bristles 21 extend from the front surface 23.

Figures 2, 3:
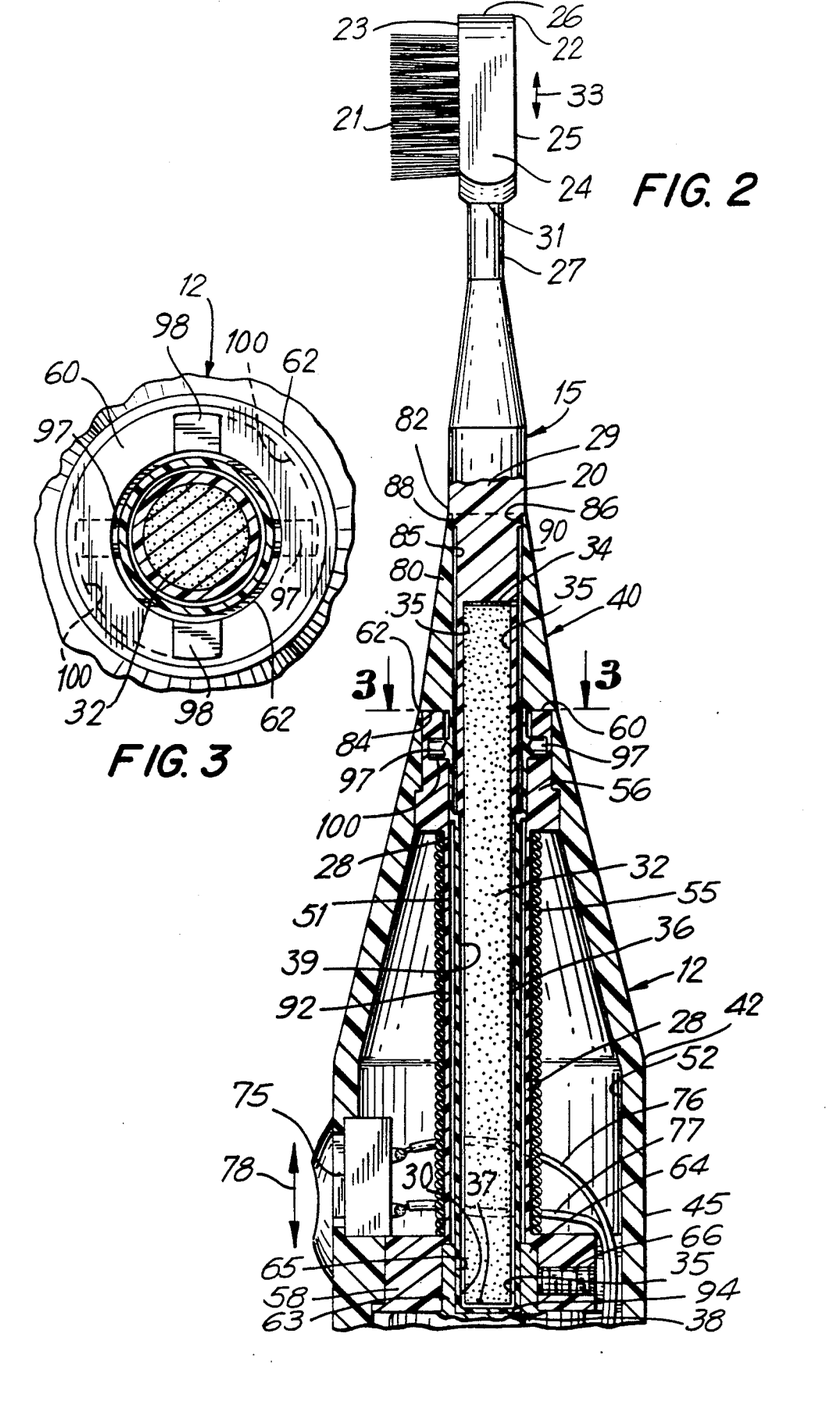
FIG. 2 is an enlarged section through the ultrasonic power means and implement of FIG. 1 taken along the lines 2—2.
FIG. 3 is a sectional view of the ultrasonic apparatus of FIG. 2 taken along lines 3—3.

The closure means 38 is provided to communicate with the body portion 20 or in conjunction with rigidly and removably mounting means 40 as hereinafter described. The closure means 38 includes a rear end portion 28 that may be coupled to the body portion 20 at one end thereof and may be in the form of a neck portion which is hollow and provided with a centrally disposed opening or cavity 30 terminating in a bottom surface or rear end 35. A resilient material may be provided on the ultrasonic implement 15 so that the same power means 12 may be utilized for massaging the gums as may be necessary. Accordingly, each toothbrush implement 15 includes bristles 21 acting as the oral contact portion for the user. An elongated member 32 of magnetostrictive material extends within the opening 30 and is coupled at one end 34 to the body portion 20 in vibration transmitting relationship as by an epoxy in the cavity or recess 35 dimensioned to receive the epoxy and elongate member 32 therein. The elongated member 32 is coaxial with the longitudinal axis of the body portion 20 and has an outer surface 36 and terminates in a rear end 37.

The closure means 38 may be coupled or affixed to the body portion 20 at the rear or distal end 28 to seal the elongated member 32 within the body portion 20, wherein the elongated member 32 is sealed for preventing moisture and water from entering the implement 15 Illustrated in FIG. 2 is a preferred embodiment in which the closure means 38 extends from the mounting means 40 such that no vibratory energy will be transmitted to the rear end portion 28 and no additional loading occurs on the body portion 20. Accordingly, the elongated body portion 20 has affixed thereto at one end an elongated vibrating member or element 32, such as of ferrite, magnetostrictive or piezoelectiic material, which can be oscillated In the illustrated embodiment, the elongated member is completely enclosed in a nonmagnetic, fluid-impervious material, such as plastic, and forms with the bristles 21 a unitary assembly which approximates the size and shape of an ordinary manual toothbrush and which may be economically produced so as to be disposable when the bristles 21 wear out.

In the illustrated embodiment, the implement 15 comprises the elongated ferrite member or element 32, or any other material capable of mechanically elongating when subjected to a magnetic field. In view of the relative dimensions of the ferrite member 32, it will be seen that upon insertion in a suitably oriented magnetic field, a significant elongation of the ferrite element 32 will occur. Consequently, upon application thereto of a magnetic field whose magnitude varies the length of the member 32 will similarly vary. In accordance with known principles, the member 32 is made to be of a length equal substantially to an integral number of quarter wavelengths in the material at the driving frequency. In this manner, maximum conversion of energy from the magnetic field to mechanical vibration is achieved. As noted hereinabove, other forms of electrical to mechanical transducers, e.g. piezoelectric, magnetostrictive, may also be employed in accordance with the present invention Rigidly affixed to one end of the ferrite element 32, such as by epoxy is the body portion 20. The body portion 20 may be formed of any suitable material capable of supporting vibrations transmitted thereto from the member 32, many metals and hard plastics are suitable for this purpose. However, to operate most efficiently, the body portion 20 should be made equal in length to an integral number of half-wavelengths in the material at the frequency of vibration. A suitable material enabling the length of the body portion 22 to be maintained within reasonable limits is Noryl, but it will be understood that other materials may also be used.

Preferably, the body portion 20 is formed of at least two sections, one being an output section 27 for amplification of the longitudinal vibrations applied to its input section 29 by the member 32. The two sections 27 and 29 are of differing diameter. The transition from the larger to the smaller diameter occurs at a nodal point of vibration, that is, a point along a member wherein longitudinal motion is a minimum. In a uniform diameter element one-half wavelength long such a node would occur at the quarter-wave point, half way between the ends. By locating the transition point at a nodal plane, proper acoustic impedance transformation takes place and an increased longitudinal amplitude of vibration is obtained at the output end 31 which is coupled to the brush head 22. The body portion 20 is of a length substantially equal to an integral number of quarter wavelengths at the ultrasonic frequency.

The power member 12 is a generally cylindrical element preferably formed of an electrically insulating and fluid impervious plastic material, which is provided with the central or axial bore 39 extending axially therein. The outer dimensions of the power member 12 are made such as to be comfortably held in the hand without causing fatigue The axial bore 39 is dimensioned for receiving in close fitting engagement one end of the ultrasonic implement 15.

The rigidly and removably mounting means 40 is provided for holding the ultrasonic implement 15 within the power member 12 with sufficient force to prevent removal during use, but to allow ready removal by hand. Alternating electrical signals are supplied to suitable elements within the power member 12 to drive the vibrating element 32 With the ultrasonic implement 15 positioned in the power member 12 and alternating electrical signals at an ultrasonic frequency supplied thereto from an oscillator or generator of convenient form, longitudinal vibrations in the direction of two headed arrow 33 are induced in the transducer portion 32 of the ultrasonic implement 15, which in turn vibrates the brush head 22 and bristles 21. The unique mounting means 40 is substantially free from absorbing ultrasonic energy into the power member 12 leaving the transducer element 32 free to transmit its energy to the bristles 21.

In family use for example, a single power member 12 and oscillation generator would be supplied, together with a number of ultrasonic implements, one for each member of the family. Each user simply inserts his own personal brush implement into the power handle prior to cleaning his or her teeth.

While the implement 15 is being manually moved over the tooth surfaces, much in the manner in which conventional brushing is performed, the body portion 20 is vibrated at an ultrasonic rate in its longitudinal direction, as indicated by the two headed arrow 33 in FIG. 2. Since the bristles 21 are carried in the body portion 20, they too vibrate at the ultrasonic frequency. Accordingly, as the bristles 21 pass over the tooth surfaces and across the interproximal areas, the ends thereof are vibrating at an ultrasonic rate to provide improved cleaning results. It has been found that with the application of ultrasonic vibrations to the ultrasonic implement 15 at a frequency in the order of from 20,000 to 50,000 cycles per second, there are obtained at the tooth and gingival surfaces improved cleaning results not obtainable with manual or conventional motor driven toothbrushes.

A typical ultrasonically driven toothbrush in accordance with the present invention may have a bristle stroke of about 0.001" and would operate at a frequency of 20,000 cycles per second. This calculates out to a peak velocity at the bristle tips of approximately 5 feet per second and distance traveled by a bristle tip of about 20 inches per second.

The ultrasonically driven brush however, does differ from motor driven brushes in that both the repetition rate of the bristle motion and the accelerations at the bristle tips are many times greater in the ultrasonic brush. These latter two factors, unique to ultrasonic actuation, are believed to be primarily responsible for the greaterly enhanced cleaning effectiveness exhibited by the ultrasonically driven brush of the present invention.

The foreign deposits normally found on teeth may be generally characterized as stain, plaque, and calculus or tartar. Stain and tartar are both adherent deposits on teeth while plaque is somewhat softer and less adherent, such as soft food deposits found in the crevices on and between teeth. Observation has indicated that hand brushing has only limited ability to remove stain and little or no effect on tartar deposits. The ultrasonically driven brush removes tartar deposits, as well as stain and interproximal deposits in a significantly superior fashion. The improved cleaning results are believed traceable to the high repetition rate of vibration and the peak accelerations available at the bristle tips in accordance with the following analysis.

It is known, from observation, that the ultrasonically vibrating bristle clusters are accompanied by a vigorous cavitational action when the cleaning area is wet. This is a direct consequence of the high peak accelerations and thus introduces a factor not present in other known tooth cleaning aids. Thus, cavitational action in the interproximal areas of the teeth would tend to remove plaque in a manner analogous to the way in which a cavitating cleaning liquid removes dirt from inaccessible regions of a complex watch mechanism.

A further cleaning action believed to occur at the tooth surfaces subjected to the action of the ultrasonically vibrating bristles is akin to a material removing method well known in industry as ultrasonic cleaning. This effect is exhibited in the presence of high frequency vibration, minute strokes of vibration, a cavitating liquid field and a low density of material-removing material in the liquid field. To obtain material removal under these conditions, it is necessary simply to press the vibratory element or elements lightly against the work surface, e.g. a tooth. Where ordinary dentifrices are used, they supply the low density of material-removing particles in the cavitating liquid field. In the event the ultrasonic brushing is carried out in the presence of a simple liquid, the process will take place as soon as appropriate material-removing particles are present. These may be provided, for example, by particles of already removed tartar or calculus suspended in the liquid. Tartar or calculus is a conglomerate or gritty particles which would serve admirably as an agent to remove further deposits. Moreover, these particles not being as hard as the tooth structure would not cause damage to the teeth.

The superiority ultrasonic tooth cleaning techniques over other brushing procedures are believed to result from a combination of the above effects which are unique to ultrasonic phenomena. As the toothbrush is moved over the tooth surfaces, the several effects will be exhibited in varying degrees However, when used daily over a period of time, it can be expected that substantially all of the tooth surfaces will experience the overall improved cleaning action to an extent that previously deposited stains, calculus and plaque will be removed and the user's mouth and teeth thereafter will be maintained in a uniquely clean state.

The power member 12 may be formed in two sections, a first or upper section 42 and a second or lower section 44 whose outer surface 45 forms the peripheral surface of the handle member or housing 12. The sections 42 and 44 may be joined together by complimentary mating threaded portions 46 or other means well known. A ring 48 of resilient material to provide a liquid tight seal may be utilized at the surface 49 and 50 of the upper section 42 and lower section 44 respectively. A tubular extension or bobbin 51 having a longitudinal hollow core or central bore 39 therein, fits within the power member 12 leaving between the inner walls 52 and 54 of sections 42 and 44, respectively an annular space extending substantially over their entire lengths. Within this annular space on the bobbin 51 is supported a wound coil 55 of insulated wire for establishing the magnetic field. The bobbin 51 has a front section or end 56 and a rear section or end 58. The front end 56 fits within the upper section 52 and has an outer surface or outward end 60 that coincides with the front surface or edge 62 of the power member 12 and is in sealed relation thereto to make it liquid impervious. The rear section 58 is enlarged and engages the inner wall 52

Restraining means 63 is provided in the form of a tubular extension 64 having a reduced inner diameter portion or seat 65 sized to snugly receive the rear end 30 of the ultrasonic implement 15 to retain same in releasably fixed relationship with respect thereto The tubular extension 64 may be contained within the rear section 58 as by a set screw 66 or other means.

Figure 4:
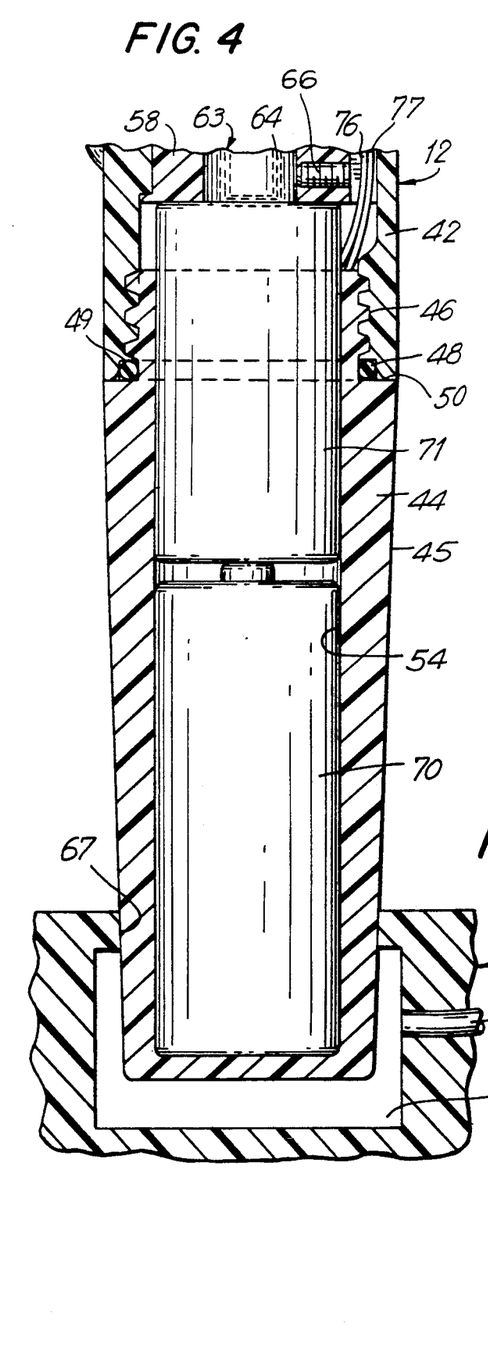
FIG. 4 is an enlarged section through the ultrasonic power means of FIG. 1 taken along the lines 4—4.

Base 16 as illustrated in FIG. 4, includes an aperture 67 for receiving therein one end of the power member 12 and recharging means 68 well known in the art to recharge the battery 70 contained in the power member 12. A converting circuit also known as an oscillator or generator 71, known in the art is mounted within the power member 12. The converting circuit arrangement 71 may utilize the A.C. power obtained from a conventional wall outlet, not shown, or from the relatively low voltage rechargeable battery means 70. When using the battery the converting circuit 68 rectifies and changes the A.C. voltage appearing at the wall outlet to a D.C. charging voltage for the rechargeable battery 70 disposed in the power member 12. As long as the power member 12 is positioned on the base member 16 and plug 72 connected by line cord 74 is plugged into a standard electrical outlet, battery 70 is trickle charged so that it maintains its peak voltage, which is a relatively low D.C. voltage preferably 9 to 12 volts. Base member 16 may also provided with openings or recesses, which firmly holds the ultrasonic toothbrushs 17, 18, and 19 in addition to the power member 12 in position on the recharging base member 16 as illustrated in FIG. 1.

A thumb switch 75 may be provided on the exterior of the power member 12 for opening or closing the coil circuit to control the supply of power to the ultrasonic implement 15. The thumb switch may be a slide type as illustrated by arrow 78 or one in which it is depressed to open the circuit. The switch 75 is connected by wires 76 and 77 to the generator 68 which is in turn connected to the battery 70 in a conventional manner. Alternatively, switch means (not shown) may be provided within the bore 39 to be actuated upon insertion of an ultrasonic implement 15 and conversely deactivated upon removal of the insert. By such means, power waste is minimized.

Accordingly the complete assembly for use in the home would include, suitable source of alternating electrical energy and D.C. polarizing current. Such a source would be provided, for example, by the oscillator or generator 71 capable of producing electrical oscillation at a frequency in the ultrasonic range e.g., between 20,000 and 50,000Hz per second. Various types of such converter means or oscillators are known for converting a source of electrical energy to a relatively low D.C. voltage for operating the ultrasonic power source and it is not believed necessary to describe the details herein.

Accordingly, electrical oscillations and direct current from the generator 71 are coupled via wires (not shown) to the coil 55 that provides the alternating driving magnetic fields which cause the magnetostrictive member 32 to move in the direction of double headed arrow 33 as the polarity of the driving current appearing in coil 55 changes direction, in a known manner. There is thus established in the bore 39 of the power member 12 a magnetic field whose magnitude changes at an ultrasonic rate. Upon insertion of the ultrasonic implement 15 the magnetostrictive member 32 is positioned within the magnetic field and in well known manner, provides a mechanical longitudinal vibration at the frequency of the magnetic field. This vibration is transmitted via the body portion or connecting member 20 to the brush head 22 and the bristles 21. Since the power member 12 is isolated from the longitudinal motion of magnetostrictive member 32 by the mounting means 40 no vibrations are coupled therethrough and no damping thereof occurs when the assembly is held in the hand of the user.

Furthermore, inasmuch as relatively low power is required and the average brushing procedure takes only a matter of minutes, the heat generated in the ferrite member 32 is insufficient to cause any damage to the apparatus itself or to provide any discomfort to the user.

In accordance with the present invention, however, relatively low frequency, small amplitude vibrations are employed to drive a brushing implement which, as in the case of the conventional toothbrush, is made up of a material soft with respect to the tooth surfaces. The various plastics such as nylon or natural bristles, are suitable for this purpose The use of relatively soft bristle materials in combination with low energy ultrasonic vibrations renders the use of the invention perfectly safe, whereby it may be regularly employed by average persons without any special training or skill. Extended periods of application of ultrasonic energy to the tooth and gingival surfaces in accordance with the present invention will have no deleterious effect on these surfaces.

In addition to the superior cleaning action provided by the ultrasonic energy, several auxiliary benefits of the ultrasonic action have been noted. The micro-massage of the gingival tissue, contributes significantly to overall dental health. The ultrasonic action also results in partial sterilization of bacterial-laden areas of the mouth and provides more intimate application of chemical or other agents that may be contained in a dentifrice or other fluids.

Cavitational action requires for its support a substantially solid film of a liquid capable of supporting cavitation between the tip of the cleaning member and the tooth surface to be cleaned. This fluid film may be provided by the natural fluids in the mouth, emission of which is stimulated during the brushing procedure, or if desired, additional fluid, such as plain water, or a dentifrice may be taken into the mouth prior to the beginning of the brushing procedure.

The mounting means 40 provides a rigid mounting arrangement for the ultrasonic implement 15 while simultaneously the contact portion in the form of the bristles 21 are free to receive the transmitted vibrations while the ultrasonic power member 12 is not absorbing any ultrasonic energy due to the manner in which the mounting means is constructed. The mounting means 40 also permits the exchangeable toothbrush implement 15 to be removed from the ultrasonic power means 12 with a relatively small separating force therebetween. The mounting means 40 includes collar means or jaw member 80 circumferentially disposed around and connected at substantially the front end 82 thereof to the body portion 20 at approximately a node of longitudinal vibration so as to maintain the ultrasonic energy substantially isolated from transmission to the collar means 80. The collar means 80 includes the front end 82 and a rear end 84' with an axially extending opening 85 for permitting the body portion 20 to extend axially therethrough. At the node of longitudinal motion there is radial motion on the body portion 20 and due in part to the mass of the collar means 80 the energy is readily absorbed therein without imparting ultrasonic energy thereto that is obvious to the user of the apparatus 10.

The rear end 84 will extend in overlapping relationship to the front end 60 of front section 56 and surface 62 of the power member 12. A shoulder 86 is provided between ends 82 and 84 and communicating with the opening 85. The shoulder 86 is dimensioned to extend in engagement with the body portion 20 at approximately a node of longitudinal vibration therein as by a force fit or mechanically coupled thereto in a sealed manner. The shoulder 86 is illustrated at the front end 82 of the collar means 80. The body portion 20 may be provided with a seat 88 adapted to receive the shoulder thereon. The shoulder, 86 and the seat 88 extend circumferencially and in telescopic relationship to each other and the longitudinal length of the shoulder 86 is small relative to the longitudinal length of the collar means 80 so as to provide a minimal contact area therebetween whereby the vibratory energy is maintained substantially isolated from transmission to the collar means 80.

The collar means 80 is joined to the body portion by bonding or the like or integrally formed with the body portion 20. The collar means 80 has as outer surface 90 adapted to be gripped by the user thereof during insertion and removal of the ultrasonic implement 15 with the ultrasonic power means 12. The outer surface 90 is tapered outwardly from the front end 82 to the rear end 84. The collar means 80 may be connected to the closure means 38 at the end thereof. In this form the closure means 38 includes the elongated hollow neck portion or extension 28 extending longitudinally from the rear end 84 of the collar means 80 and having the inner wall surface or diameter 30 an outer wall surface or diameter 92. The neck portion 28 may terminate at one end in the form of a disc or plate 94 that seals off the neck portion 28 to prevent moisture and liquid from entering therein. The outer diameter or dimension of the member 32 is smaller than the diameter 39 to provide a minimum space therebetween. The outer wall surface 92 of section 28 is adapted to be received within the cavity 30 with minimal space therebetween.

Stability and support for the rear end of the neck portion 28 is provided by the restraining means 63. In this manner there is provided a unitary assembly for an ultrasonic implement 15 that is readily interchangeable and to the user the appearance of a toothbrush is maintained with no indication that an ultrasonic motor is contained in the ultrasonic implement 15. Each implement 15 may be fabricated in a set of colors for ready identification by each user.

To retain the ultrasonic implement 15 in fixed relationship to the power member 12 during use of the toothbrush assembly 10 there is provided locking means 95. The locking means 95 includes at least one longitudinally outwardly extending pin or projection 97 being disposed at the circumference of the neck portion 28 to function as keying guide means in conjunction with a longitudinal channel 98 as illustrated in FIG. 3, from the front end or distal edge 60 of the ultrasonic power means 12 with the other end of the longitudinal channel terminating in a relatively short channel 100 disposed transverse to the longitudinal channel 98. In use the toothbrush implement 15 is aligned with each projection 97 engaging longitudinal channel 98 dimensioned to cooperate with each other so that the outwardly extending projection 97 slidably engages and enters elongated channel 98 so that when it is fully inserted as illustrated in FIG. 2.

When the toothbrush implement is rotated less than a full turn with respect to the power means 12, the outwardly extending projections 97 become seated into the relatively short transverse channels 100 and the projections 97 are in coupling relation. It being understood that the projections 97 may be dimensioned to frictionally engage the channels 98 so that the toothbrush implement 15 may be engaged and removed from the ultrasonic power means 12 with a relatively small separating force therebetween.

Figure 5:
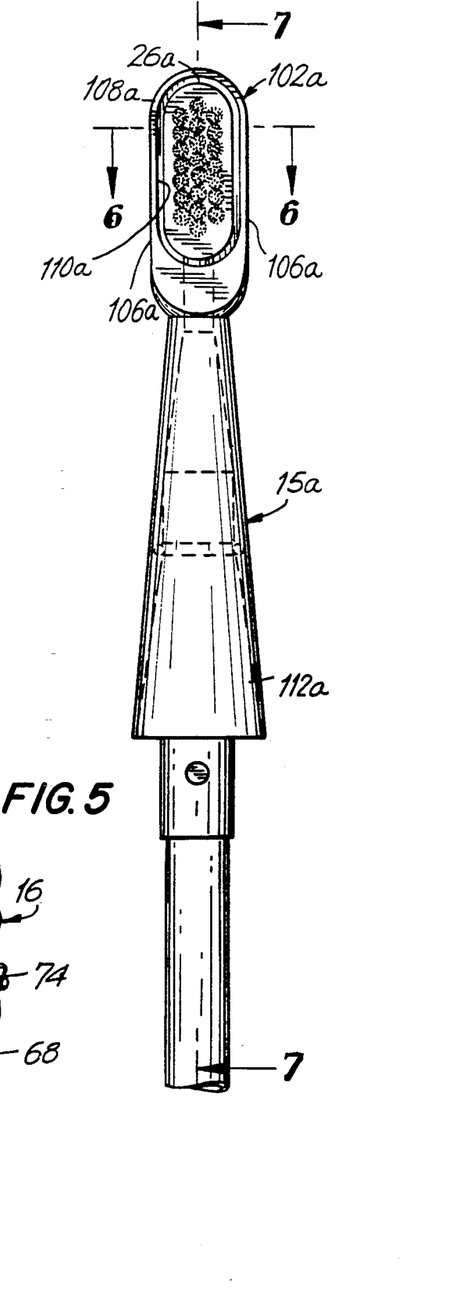
FIG. 5 is an assembled view, in partial cross section, of another embodiment of an ultrasonic implement according to the present invention.
Figure 6:
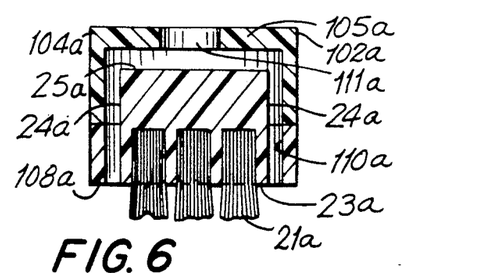
FIG. 6 is a section through the ultrasonic implement of FIG. 5 taken along lines 6—6.
Figure 7:
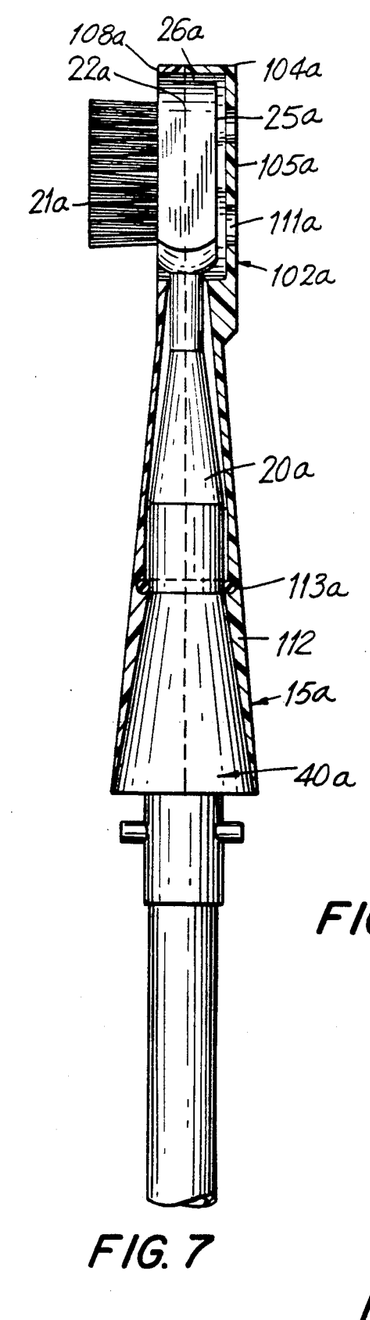
FIG. 7 is a partial section through the ultrasonic implement of FIG. 5 taken along the lines 7-7.

Referring now to FIGS. 5, 6 and 7 there is illustrated another embodiment of the invention in which the ultrasonic implement 15a may be of the construction as illustrated in FIGS. 1-4 but further includes guard means 102a mounted on the implement 15a thereby substantially preventing vibratory energy to be transmitted from the body portion 20a to the user. In this manner vibratory energy from the oral contact portion in the form of the bristles 21a is only transmitted to the user.

The guard means 102a may include a cover or hood 104a extending in substantially spaced relation to the body portion 20a. The brush head 22a is adapted to fit within the hood 104a. The hood 104a has a head 105a and a rim 106a extending peripherally and downwardly therefrom and terminating in a lip 108a that will generally coincide with the front surface 23a of the brush head 22a. The side surfaces 24a and top surface 25a are maintained in spaced relationship to the inner wall surface 110a of the rim 106a. The bristles 21a extend beyond the rim lip 108a to freely engage the teeth of the user.

The guard means 102a may take other forms, but its intended purpose is to limit the contact in the oral cavity of the user to the bristles 21a. A plurality of apertures 111a extending through the head 105a of the hood 104a and are provided to facilitate the removal of any dentifrice accumulating in the space between the brush head 22a and the guard means 102a.

The guard means 102a may also include a leg 112a that is formed with the hood 104a and extends in telescopic relation to the body portion 20a which is supported from the mounting means 40a which is free of any ultrasonic mechanical vibration. Due to the length of the body portion 20a a resilient support element 113a may be interposed to maintain the spaced relationship between the body portion 20a and guard means 102a.

Figure 8:
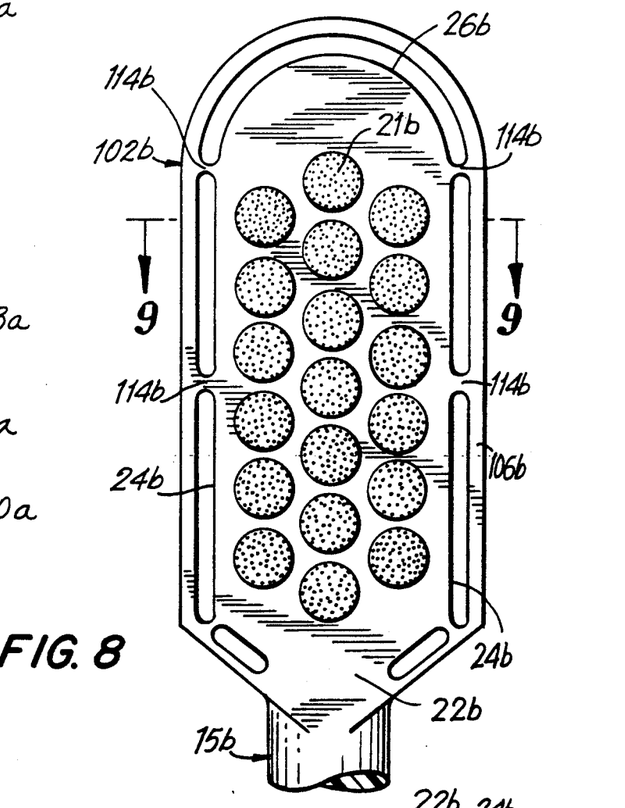
FIG. 8 is an enlarged framentary view of an alternate embodiment of an ultrasonic implement.
Figure 9:
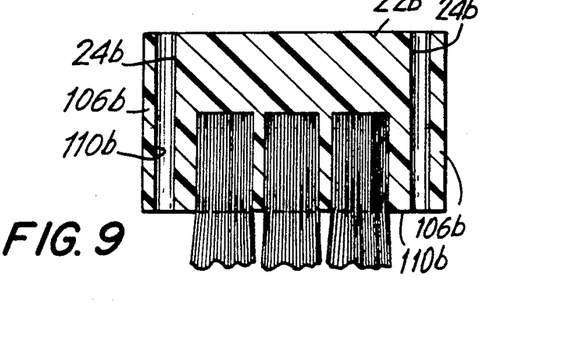
FIG. 9 is a sectional view of the ultrasonic implement of FIG. 8 taken along lines 9—9.

FIGS. 8 and 9 illustrate another embodiment of the invention in which the ultrasonic implement 15b includes guard means 102b in the form of a circumferentially extending rim 106b that is mounted in a substantially acoustically isolated manner to the brush head 22b. The same end purpose as discussed with respect to FIGS. 5, 6 and 7 is accomplished. To support the rim 106b spaced apart tabs or ears 114b are provided from the surfaces 24b and 26b to acoustically isolate the rim 106b. A space between the rim 106b inner wall 110b and the side surface 24b is maintained. The bristles 21b remain in clusters and in spaced relationship to each other.

Hereinbefore has been disclosed an ultrasonic toothbrush apparatus capable of being exchanged with another unit with a minimum of effort and force. It will be understood that various changes in the details, materials, arrangement of parts and operating conditions which have been hereinbefore described and illustrated in order to explain the nature of the invention may be made by those skilled in the art within the principles and scope of the instant invention.

Having thus set forth the nature of the invention what is claimed is:

1. An ultrasonic toothbrush apparatus comprising:
   A. an exchangeable toothbrush implement including;
      a. an elongated body portion of vibration transmitting material having an oral contact portion disposed on one distal end of said body portion,
      b. the other end of said body portion being hollow and provided with a centrally disposed opening,
      c. an elongated member of magnetostrictive material having one end thereof extending within said opening and coupled to said body portion in vibration transmitting relationship,
   B. an ultrasonic power means for supplying vibratory energy in the ultrasonic range, said power means including;
      i) an elongated hollow housing having an opening at one end for receiving said toothbrush implement, and
      ii) mating locking means disposed proximate said one end of said elongated hollow housing;
   C. means for rigidly and removably mounting said exchangeable toothbrush implement upon said ultrasonic power means for transmitting vibratory energy through said body portion to said oral contact portion substantially free from absorbing ultrasonic energy in said ultrasonic power means including;
      i) locking means, said locking means cooperating with said mating locking means disposed upon said power means to retain said toothbrush implement in fixed relationship to said ultrasonic power means during use of said toothbrush, said exchangeable toothbrush implement being removed from said ultrasonic power means with a relatively small separating force therebetween; and
   D. closure means encompassing said elongated magentrostrictive member of said body portion wherein said elongated magnetostrictive member is sealed for preventing moisture and liquid from entering said implement.

2. An ultrasonic toothbrush according to claim 1 wherein a. said elongated member has a length equal substantially to an integral number of quarter wavelengths of the ultrasonic vibration frequency, and b. said body portion is of a length substantially equal to an integral number of quarter wavelengths of the ultrasonic vibration frequency.

3. An ultrasonic toothbrush according to claim 1 wherein said magnetostrictive material is a ferrite.

4. An ultrasonic toothbrush according to claim 1 wherein said locking means includes:

a. at least one longitudinally outwardly extending projection being disposed at the circumference of said toothbrush implement to function as keying guide means; and b. a longitudinal channel having one end extending inwardly from one distal edge of said ultrasonic power means with the other end of said longitudinal channel terminating in a relatively short channel disposed transverse to said longitudinal channel, said toothbrush implement outwardly extending projection and said longitudinal channel being adapted to cooperate with each other, said outwardly extending projection slidably engaging said ultrasonic power means elongated channel, whereby, when said toothbrush implement is rotated with respect to said power means sufficient for said implement outwardly extending projection to be seated into said relatively short transverse channel said implement projection is in coupling relation therewith.

5. An ultrasonic toothbrush according to claim 1, wherein said ultrasonic power means for supplying vibratory energy in the ultrasonic range further includes:

a. elongated coil means adapted to receive therein a portion of said elongated magnetostrictive member, said elongated member being retained in said housing, and b. an ultrasonic generator means for supplying vibratory energy in the ultrasonic range disposed within said housing, said ultrasonic generator means being adapted to be coupled to said coil means and a source of electrical energy.

6. An ultrasonic toothbrush according to claim 5 wherein said coil means is supported on a bobbin having a longitudinal hollow core disposed therein adapted to slidably receive said magnetostrictive member of said toothbrush implement.

7. An ultrasonic toothbrush according to claim 1 wherein said ultrasonic power means comprises:

a. a relatively low voltage rechargeable battery means, and b. electrical circuit means for providing said vibratory ultrasonic energy connected to said battery means.

8. An ultrasonic toothbrush according to claim 7 wherein said ultrasonic power means comprises converter means for converting a source of electrical energy to a relatively low D.C. voltage for operating said ultrasonic power source.

9. An ultrasonic toothbrush according to claim 1, wherein said mounting means includes collar means connected at substantially said other end of said body portion at approximately a node of longitudinal vibration so as to maintain said ultrasonic energy substantially isolated from transmission to said collar means, said collar means being adapted to cooperate with a mating ledge provided proximate one distal end of said power means.

10. An ultrasonic toothbrush according to claim 9 wherein said collar means includes:

a. a front end and a rear end with an axially extending opening for permitting said body portion to extend therethrough, and b. a shoulder provided between said ends and communicating with said opening, said shoulder dimensioned to extend in engagement with said body portion at approximately said node of longitudinal vibration.

11. An ultrasonic toothbrush according to claim 10 wherein said shoulder is at said front end of said collar means.

12. An ultrasonic toothbrush according to claim 10 wherein said collar means is joined to said body portion by bonding or the like.

13. An ultrasonic toothbrush according to claim 10 wherein said collar means is integrally formed with said body portion.

14. An ultrasonic toothbrush according to claim 10 wherein a. said body portion is provided with a seat adapted to receive said shoulder thereon; and b. said shoulder and said seat extend circumferentially and in telescopic relationship to each other and said shoulder is small relative to the longitudinal length of said collar means so as to provide a minimal contact area therebetween whereby said vibratory energy is maintained substantially isolated from transmission to said collar means.

15. An ultrasonic toothbrush according to claim 10 wherein said collar means has an outer surface adapted to be gripped by the user thereof during insertion and removal from said ultrasonic power means.

16. An ultrasonic toothbrush according to claim 15 wherein said outer surface is tapered outwardly from said front end to said rear end.

17. An ultrasonic toothbrush according to claim 10 wherein a. said closure means includes a hollow neck portion extending longitudinally from said rear end of said collar means; and b. at least one outwardly extending projection being disposed on said neck portion for use in quickly releasing said ultrasonic implement from said ultrasonic power means.

18. An ultrasonic toothbrush according to claim 10 further including guard means connected to said mounting means for permitting ultrasonic energy to be transmitted to the user from said oral contact portion.

19. An ultrasonic toothbrush according to claim 18 wherein said guard means includes a hood extending in substantially spaced relation to said body portion.

20. An ultrasonic toothbrush according to claim 19 wherein said guard means includes a plurality of apertures extending through said hood to facilitate the removal of any dentifrice accumulating in the space between said body portion and said guard means.

21. An ultrasonic toothbrush according to claim 1, wherein said body portion is fabricated of a non-magnetic material capable of transferring ultrasonic energy, is coaxial with the longitudinal axis of said elongated magnetostrictive member and includes an elongated acoustic impedance transformer means for amplifying vibrations provided by said magnetostrictive member, said elongated acoustic impedance transformer means is coupled at one end to one section of said body portion and at the other end to the implement section of said body portion by means of an epoxy adhesive.

22. A quick release ultrasonic implement for use with a source of vibratory ultrasonic energy comprising:
   A. an elongated body portion of vibration transmitting material having an element disposed on one distal end of said body portion,
   B. the other end of said body portion being hollow and provided with a centrally disposed opening,
   C. an elongated member of magnetostrictive material extending within said opening and coupled at one end to said body portion in vibration transmitting relationship,
   D. means for rigidly and removably mounting said body portion to said source of ultrasonic energy for transmitting vibratory energy through said body portion to said element wherein said vibratory energy is substantially isolated from transmission to said mounting means, including locking means, said locking means having;
      i) at least one longitudinally outwardly extending projection being disposed at the circumference of said element to function as a keying guide means,; and
      ii) a longitudinal channel extending inwardly from said ultrasonic power means with one end of said longitudinal channel terminating in a relatively short channel disposed transverse to said longitudinal channel,
   said implement outwardly extending projection and said longitudinal channel being adapted to cooperate with each other so that said outwardly extending projection slidably engages said ultrasonic power means elongated channel when said implement is rotated with respect to said power means sufficient for said implement outwardly extending projection to be seated into said relatively short transverse channel when said implement projection is in coupling relation therewith; and
   E. closure means encompassing said elongated magnetostrictive member of said body portion wherein said elongated magnetostrictive material is sealed within said body portion for preventing moisture and liquid from entering said implement.

23. A quick release ultrasonic implement according to claim 22 wherein said elongated member has a length equal substantially to an integral number of quarter wavelengths in the material at the frequency said elongated member is calculated to vibrate.

24. A quick release ultrasonic implement according to claim 22 wherein said body portion is of a length substantially equal to an integral number of quarter wavelengths of the ultrasonic vibration frequency.

25. A quick release ultrasonic implement according to claim 22 wherein said body portion is fabricated of a nonmagnetic material capable of transferring ultrasonic energy.

26. A quick release ultrasonic implement according to claim 22 wherein said body portion is coaxial with the longitudinal axis of said elongated member.

27. A quick release ultrasonic implement according to claim 22 wherein said magnetostrictive material is a ferrite.

28. A quick release ultrasonic implement according to claim 20, wherein the portion between said one distal end and the other end of said body portion comprises an acoustical impedance transformer for amplifying vibrations provided by said magnetostrictive member.

29. A quick release ultrasonic implement according to claim 22 wherein said member is coupled to said body portion by means of an epoxy adhesive.

30. A quick release ultrasonic implement according to claim 22 wherein said ultrasonic implement is structured to be disposable and interchangeable by the user.

31. A quick release ultrasonic implement according to claim 22 wherein said mounting means includes collar means rigidly connected at substantially one end thereof to said body portion at approximately a node of longitudinal vibration so as to maintain said ultrasonic energy substantially isolated from transmission to said mounting means.

32. A quick release ultrasonic implement according to claim 31 wherein said collar means includes:
   a. a front end and a rear end with an axially extending opening for permitting said body portion to extend therethrough; and
   b. a shoulder provided between said ends and communicating with said opening, said shoulder dimensioned to extend in engagement with said body portion at approximately said node of longitudinal vibration.

33. A quick release ultrasonic implement according to claim 32 wherein said shoulder is at said front end of said collar means.

34. A quick release ultrasonic implement according to claim 32 wherein said collar means is joined to said body portion by bonding.

35. A quick release ultrasonic implement according to claim 32 wherein said collar means is integrally formed with said body portion.

36. A quick release ultrasonic implement according to claim 32 wherein
   a said body portion is provided with a seat adapted to receive said shoulder thereon; and
   b. said shoulder and said seat extend circumferentially and in telescopic relationship to each other and said shoulder is small relative to the longitudinal length of said collar means so as to provide a minimal contact area therebetween whereby said vibratory energy is maintained substantially isolated from transmission to said collar means.

37. A quick release ultrasonic implement according to claim 32 wherein said closure means is connected to said mounting means.

38. A quick release ultrasonic implement according to claim 32 wherein said collar means has an outer surface adapted to be gripped by the user thereof during insertion and removal from said source of ultrasonic energy.

39. A quick release ultrasonic implement according to claim 38 wherein said outer surface is tapered outwardly from said front end to said rear end.

40. An ultrasonic apparatus comprising:
   A. an exchangeable implement containing an elongated magnetostrictive member,
   B. closure means for sealing said magnetostrictive member of said implement for preventing liquid from entering therein,
   C. an ultrasonic power means for supplying vibratory energy in the ultrasonic range having a receiving end;
   D. means for rigidly and removably mounting said exchangeable implement upon said ultrasonic power means receiving end for efficiently transmitting vibratory energy from said elongated member through said exchangeable implement substantially free from absorbing ultrasonic energy in said ultrasonic power means, with a relatively small separating force therebetween, including locking means on said implement operatively connected to said mounting means to cooperate with said power means to retain said implement in fixed relationship to said ultrasonic power means during use of said apparatus.

41. An ultrasonic apparatus according to claim 40 wherein said locking means includes;
   a. at least one longitudinally outwardly extending projection being disposed at the circumference of said implement to function as keying guide means; and
   b. a longitudinal channel extending inwardly from said ultrasonic power means with one end of said longitudinal channel terminating in a relatively short channel disposed transverse to said longitudinal channel,
   said implement outwardly extending projection and said longitudinal channel being adapted to cooperate with each other so that said outwardly extending projection slidably engages said ultrasonic power means elongated channel when said implement is rotated with respect to said power means sufficient for said implement outwardly extending projection to be seated into said relatively short transverse channel when said implement projection is in coupling relation therewith.

42. An ultrasonic apparatus according to claim 40 wherein said ultrasonic power means for supplying vibratory energy in the ultrasonic range includes:
   a. an elongated hollow housing having an opening at one end for receiving said implement,
   b. elongated coil means adapted to receive therein a portion of said elongated member, said elongated member being retained in said housing; and
   c. said ultrasonic power means for supplying vibratory energy in the ultrasonic range disposed within said housing, said power means being adapted to be coupled to said coil means and a source of electrical energy.

43. An ultrasonic apparatus according to claim 40 wherein said ultrasonic implement includes collar means rigidly connected at said other end of said body portion at approximately a node of longitudinal vibration along said implement so as to maintain said ultrasonic energy substantially isolated from transmission to said collar means when coupled to said ultrasonic energy source.

44. An ultrasonic apparatus according to claim 43 wherein said collar means includes:
   a. a front end and a rear end with an axially extending opening for permitting said implement to extend therethrough,
   b. a shoulder provided between said ends and communicating with said opening, said shoulder dimensioned to extend in engagement with said implement at approximately said node of longitudinal vibration; and
   c. said shoulder and said seat extend circumferentially and in telescopic relationship to each other and said shoulder is small relative to the longitudinal length of said collar means so as to provide a minimal contact area therebetween whereby said vibratory energy is maintained substantially isolated from transmission to said collar means.

45. An ultrasonic toothbrush apparatus comprising:
   a) an exchangeable toothbrush implement including
      i) an elongated body portion of vibration transmitting material having an oral contact portion disposed on one distal end of said body portion,
      ii) to other end of said body portion being hollow and provided with a centrally disposed opening,
      iii) an elongated member of magnetostrictive material having one end thereof extending within said opening and coupled to said body portion in vibration transmitting relationship;
   b) an ultrasonic power means for supplying vibratory energy in the ultrasonic range;
   c) means for rigidly and removably mounting said exchangeable toothbrush implement upon said ultrasonic power means for transmitting vibratory energy through said body portion to said oral contact portion substantially free from absorbing ultrasonic energy from said ultrasonic power means, said exchangeable toothbrush implement being removed from said ultrasonic power means with a relatively small separating force therebetween, said mounting means including a collar means connected at substantially said other end of said body portion at approximately a node of longitudinal vibration so as to maintain said ultrasonic energy substantially isolated from transmission to said collar means, said collar means including;
      i) a front end and a rear end with an axially extending opening for permitting said body portion to extend therethrough, and
      ii) a shoulder provided between said front end ends communicating with said opening, said shoulder dimensioned to extend in engagement with said body portion at approximately said node of longitudinal vibration and is adapted to cooperate with a mating ledge provided on said ultrasonic power means; and
   d) closure means encompassing said elongated magnetostrictive member of said body portion wherein said elongated magnetostrictive member is sealed for preventing moisture and liquid from entering said implement.

46. An ultrasonic toothbrush according to claim 45, wherein said shoulder is at said front end of said collar means.

47. An ultrasonic toothbrush according to claim 45, wherein said collar means is joined to said body portion by bonding or the like.

48. An ultrasonic toothbrush according to claim 45, wherein said collar means is integrally formed with said body portion.

49. An ultrasonic toothbrush according to claim 45, wherein
   a. said body portion is provided with a seat adapted to receive said shoulder thereon; and
   b. said shoulder and said seat extend circumferentially and in telescopic relationship to each other and said shoulder is small relative to the longitudinal length of said collar means so as to provide a minimal contact area therebetween, whereby said vibratory energy is maintained substantially isolated from transmission to said collar means.

50. An ultrasonic toothbrush according to claim 45, wherein said collar means has an outer surface adapted to be gripped by the user thereof during insertion and removal from said ultrasonic power means.

51. An ultrasonic toothbrush according to claim 50, wherein said outer surface is tapered outwardly from said front end to said rear end.

52. An ultrasonic toothbrush according to claim 45, wherein said closure means includes:
   a) a hollow neck portion extending longitudinally from said rear end of said collar means, and
   i) at least one outwardly extending projection for use in quickly releasing said ultrasonic implement from said ultrasonic power means.

53. An ultrasonic toothbrush according to claim 45 further including guard means connected to said mounting means for permitting ultrasonic energy to be transmitted to the user from said oral contact portion.

54. An ultrasonic toothbrush according to claim 53 wherein said guard means includes a hood extending in substantially spaced relation to said body portion.

55. An ultrasonic toothbrush according to claim 54 wherein said guard means includes a plurality of apertures extending through said hood to facilitate the removal of any dentifrice accumulating in the space said body portion and said guard means.

* * * * *